United States Patent
Ra et al.

(10) Patent No.: US 9,955,898 B2
(45) Date of Patent: May 1, 2018

(54) CANCER DIAGNOSIS METHOD USING RESPIRATORY GAS

(71) Applicants: R BIO CO., LTD., Seoul (KR); Jeong-Chan Ra, Suwon-si, Gyeonggi-do (KR)

(72) Inventors: Jeong-Chan Ra, Gyeonggi-do (KR); Soo Hyun Kim, Ohsan-si (KR)

(73) Assignees: Jeong-Chan Ra, Seoul (KR); R Bio Co., Ltd., Seoul (KR)

( * ) Notice: Subject to any disclaimer, the term of this patent is extended or adjusted under 35 U.S.C. 154(b) by 198 days.

(21) Appl. No.: 14/758,176

(22) PCT Filed: Dec. 19, 2013

(86) PCT No.: PCT/KR2013/011848
§ 371 (c)(1),
(2) Date: Jun. 26, 2015

(87) PCT Pub. No.: WO2014/104649
PCT Pub. Date: Jul. 3, 2014

(65) Prior Publication Data
US 2015/0351662 A1     Dec. 10, 2015

(30) Foreign Application Priority Data
Dec. 26, 2012 (KR) .................. 10-2012-0153283

(51) Int. Cl.
*A61B 5/08* (2006.01)
*G01N 33/574* (2006.01)
(Continued)

(52) U.S. Cl.
CPC ....... *A61B 5/082* (2013.01); *G01N 33/57488* (2013.01); *G01N 30/7206* (2013.01);
(Continued)

(58) Field of Classification Search
CPC .................................................. A61B 5/082
See application file for complete search history.

(56) References Cited

U.S. PATENT DOCUMENTS

| | | | |
|---|---|---|---|
| 5,996,586 | A | 12/1999 | Phillips |
| 2006/0054023 | A1 | 3/2006 | Raetz et al. |

(Continued)

FOREIGN PATENT DOCUMENTS

| | | |
|---|---|---|
| CN | 101013115 A | 8/2007 |
| CN | 101334399 A | 12/2008 |

(Continued)

OTHER PUBLICATIONS

Wehinger et al., "Lung cancer detection by proton transfer reaction mass-spectrometric analysis of human breath gas," International Journal of Mass Spectrometry, Jul. 2007, vol. 265, No. 1, pp. 49-59.

(Continued)

*Primary Examiner* — Christian Jang
(74) *Attorney, Agent, or Firm* — Hultquist, PLLC; Steven J. Hultquist (57) ABSTRACT

A method for diagnosing cancer, comprises detecting volatile organic compounds (VOCs) contained specifically in exhaled breath of cancer patients, and more particularly, to a method for providing information for cancer diagnosis, which comprises a step of measuring whether ionized fragments of cancer-specific VOCs, which have molecular weights of (i) 69, (ii) 131 and (iii) 181, are present in exhaled breath gas collected from patients suspected of having cancer. Cancer can be early diagnosed with high sensitivity in a non-invasive manner by use of exhaled breath sampled from cancer patients. Thus, the cancer diagnosis method can diagnose cancer in a more cost-effective and rapid manner compared to conventional cancer diagnosis methods.

6 Claims, 4 Drawing Sheets

(51) Int. Cl.
   *G01N 30/88* (2006.01)
   *G01N 30/72* (2006.01)
   *G01N 33/497* (2006.01)
   *G01N 33/00* (2006.01)

(52) U.S. Cl.
   CPC . *G01N 33/0047* (2013.01); *G01N 2030/8804* (2013.01); *G01N 2030/884* (2013.01); *G01N 2033/4975* (2013.01)

(56) References Cited

U.S. PATENT DOCUMENTS

| | | |
|---|---|---|
| 2010/0198521 A1 | 8/2010 | Haick |
| 2011/0114511 A1 | 5/2011 | Sjong |
| 2011/0277538 A1 | 11/2011 | Haick et al. |
| 2012/0179389 A1 | 7/2012 | Reisfeld et al. |

FOREIGN PATENT DOCUMENTS

| | | |
|---|---|---|
| CN | 201852800 U | 6/2011 |
| CN | 102338757 A | 2/2012 |
| JP | 2002534697 A | 10/2002 |
| JP | 2010-249647 A | 11/2010 |
| JP | 2012-510319 A | 5/2012 |
| KR | 10-2009-0024595 A | 3/2009 |
| KR | 10-1168199 B1 | 7/2012 |
| KR | 10-2012-0117802 A | 10/2012 |
| WO | 2009048739 A2 | 4/2009 |
| WO | 2010/065452 A1 | 6/2010 |

OTHER PUBLICATIONS

Toshio Takayanagi, "Environmental Spreading of Perfluorinated Surfactants and its Bioaccumulation," Bunseki, The Japan Society for Analytical Chemistry, Apr. 2006, vol. 376, pp. 170-171.
European Search Report dated Jul. 26, 2016 of corresponding European Patent Application No. 13869410.4—7 pages.
Japanese Office Action dated Jul. 12, 2016 of corresponding Japanese Patent Application No. 2015-550302—4 pages.
Chinese Office Action dated Jun. 1, 2016 of corresponding Chinese Patent Application No. 201380068473.9—6 pages.
Hong et al., "Exhaled volatile organic compounds detection in cancer diagnosis", Journal of International Oncology, May 2012, vol. 39, No. 5, pp. 370-373.
International Search Report dated Mar. 21, 2014 of PCT/KR2013/011848 which is the parent application and its English translation—4 pages.
Michael Phillips, MD et al., "Volatile markers of breast cancer in the breath", The Breast Journal, 2003, vol. 9, No. 3, pp. 184-191.
Michael Phillips, et al., "Prediction of breast cancer using volatile biomarkers in the breath", Breast Cancer Research and Treatment, 2006, vol. 99, pp. 19-21.
Hossam Haick, "Detection of lung, breast, colorectal, and prostate cancers from exhaled breath using a single array of nanosensors", British Journal of Cancer, 2010, vol. 103, pp. 542-551.

CANCER DIAGNOSIS METHOD USING RESPIRATORY GAS

TECHNICAL FIELD

The present invention relates to a method for diagnosing cancer, which comprises detecting volatile organic compounds (VOCs) contained specifically in exhaled breath of cancer patients, and more particularly, to a method for providing information for cancer diagnosis, which comprises a step of measuring whether ionized fragments of cancer-specific VOCs, which have molecular weights of (i) 69, (ii) 131 and (iii) 181, are present in exhaled breath gas collected from patients suspected of having cancer.

BACKGROUND TECHNOLOGY

Breast cancer is known as one of the most common cancer in women worldwide. However, it is known that the survival rate of breast cancer patients is higher than those of other cancer patients, when breast cancer is diagnosed early and treated by suitable methods such as surgery. Methods capable of diagnosing breast cancer include X-ray-based mammography, ultrasonic examination, diagnostic imaging techniques such as breast magnetic resonance imaging (MRI), biopsy, and breast self-examination. Mammography has disadvantages in that it is costly and uses radiation. Breast magnetic resonance imaging (MRI) is a safe method that does not use radiation, and is superior to other diagnostic imaging techniques, but incurs high costs that are an obstacle to the popular use of the breast MRI. In addition, biopsy enables accurate cancer diagnosis, but is difficult to use as an early diagnostic method, because it is costly and leaves a scar.

Recent Korean Cancer Statistics indicated that about 32,000 new thyroid cancer patients in the year 2009 occurred and thyroid cancer ranked the first among all types of cancer. Such thyroid cancer patients account for about of new cancer patients in Korea and are expected to further increase in the future. However, thyroid cancer is known to have a very good prognosis, and most thyroid cancers are completely curable, but some thyroid cancers can be very aggressive. Thus, it is important to early diagnose thyroid cancer. Diagnosis starts mainly with clinical and blood test findings and imaging evaluation, and cancer is pathologically diagnosed through fine needle aspiration biopsy or surgery. However, such diagnostic methods are all invasive, costly and not easy to carry out, and a more universal and inexpensive diagnostic method is required. Diagnosis of thyroid cancer using exhaled breath appears to be a non-invasive and inexpensive diagnostic method.

As non-invasive early diagnostic methods for cancer diseases, methods of detecting cancer-specific volatile organic compounds (VOCs) in exhaled breath of cancer patients with lung cancer, breast cancer, head and neck cancer or the like have been actively studied. However, the methods of diagnosing cancer using exhaled breath have not yet been widely used. This is because exhaled breath is mostly composed of nitrogen, oxygen, carbon dioxide and the like, and the concentration of volatile organic compounds (VOCs) in exhaled breath is as very low as nanomolar ($10^{-9}$ M) or picomolar ($10^{-12}$ M) concentration, and it is very difficult to find a cancer-specific component in these volatile organic compounds. However, with the recent development of odor sensor technologies such as electronic noses, studies on the possible use of volatile organic compounds (VOCs), contained in human exhaled breath or urine, as indicators of various diseases, particularly cancers, have been conducted.

It is known that substances caused by excessive oxidative stress cause several types of cancer, including breast cancer. Oxidative stress increases the levels of mitochondrial reactive oxygen species (ROSs), and allows these ROSs to be introduced into the cytoplasm to oxidize DNA, protein, etc. Particularly, oxidative stress causes lipid peroxidation of polyunsaturated fatty acids. Substances resulting from this lipid peroxidation are VOCs, including alkane ($C_4$-$C_{20}$) compounds, methylalkane compounds, etc., and such VOCs are transferred from cellular tissues into the blood circulation system, and some of these VOCs are exhaled as alveolar exhaled breath.

Recent studies reported that breast cancer-specific VOCs detected in exhaled breath include compounds such as alkane (nonane) and methyl alkane (5-methyl tridecane, etc.) (Micheal Phillips, MD, *The Breast Journal*, 9:184, 2003), as well as 2-propanol,2,3-dyhydro-1-phenyl-4(1H)-quinazolinone, 1-phenyl-ethanone, heptanol, isopropyl myristate, etc. (Micheal Phillips, MD, *Breast cancer Research and Treatment*, 99:19, 2006). In addition, known carcinogenic compounds, including 3,3-dimethyl pentane, 2-amino-5-isopropyl-8-methyl-1-azulene carbonitrile, 5-(2-methylpropyl) nonane, 2,3,4-trimethyl decane, 6-ethyl-3-octyl ester 2-trifluoro methyl benzoic acid (Hossam Haick, *British Journal of Cancer*, 103:542, 2010), etc., were detected in breath samples of breast cancer patients, but are difficult to apply to a diagnostic method based on breath detection.

In view of such facts, in Korea, there is an urgent need to develop a method for diagnosing breast cancer, which enables early diagnosis and is inexpensive and non-invasive.

Accordingly, the present inventors have made extensive efforts to develop an inexpensive and non-invasive method for early diagnosing cancer, and as a result, have developed a method of diagnosing cancer by analyzing breast cancer-specific volatile organic compounds (VOCs), which are contained specifically in exhaled breath of cancer patients, by use of an electronic nose based on mass spectrometry, and detecting the presence or absence of the cancer-specific volatile organic compounds in the exhaled breath, thereby completing the present invention.

SUMMARY OF INVENTION

It is an object of the present invention to provide a non-invasive method for early diagnosing cancer, which comprises analyzing volatile organic compounds contained in exhaled breath of a cancer patient.

To achieve the above object, the present invention provides a method of analyzing ionized fragments of cancer-specific VOCs in exhaled breath for diagnosing cancer, the method comprising the steps of: (a) detecting ionized fragments of cancer-specific VOCs, which have molecular weights of (i) 69, (ii) 131 and (iii) 181, in exhaled breath gas; and (b) acquiring cancer-related information based on the results of the detection.

The present invention also provides a method for providing information for cancer diagnosis, the method comprising the steps of: (a) detecting ionized fragments of cancer-specific VOCs, which have molecular weights of (i) 69, (ii) 131 and (iii) 181, in exhaled breath gas; and (b) acquiring cancer-related information based on the results of the detection.

The present invention also provides a method for providing information for cancer diagnosis, the method comprising a step of measuring whether a cancer-specific VOC selected from the group consisting of perfluorodecanoic acid, perfluoro-n-pentanoic acid, perfluorononanoic acid, perfluorooctanoic acid, perfluoro-1-heptene, perfluorocyclohexane, 1H,1H-perfluoro-1-heptanol octafluorocyclobutane and perfluoro(methylcyclohexane) is present in exhaled breath gas collected from a patient suspected of having cancer.

The present invention also provides a method of measuring a cancer-specific VOC for diagnosing cancer, the method comprising measuring whether a cancer-specific VOC selected from the group consisting of perfluorodecanoic acid, perfluoro-n-pentanoic acid, perfluorononanoic acid, perfluorooctanoic acid, perfluoro-1-heptene, perfluorocyclohexane, 1H,1H-perfluoro-1-heptanol octafluorocyclobutane and perfluoro(methylcyclohexane) is present in exhaled breath gas collected from a patient suspected of having cancer.

Other features and embodiments of the present invention will be more apparent from the following detailed descriptions and the appended claims.

DETAILED DESCRIPTION OF EMBODIMENTS OF THE INVENTION

Unless otherwise defined, all technical and scientific terms used herein have the same meaning as commonly understood by one of ordinary skill in the art to which the invention pertains. Generally, the nomenclature used herein are well known and commonly used in the art.

In one aspect, the present invention is directed to a method of analyzing ionized fragments of cancer-specific VOCs in exhaled breath for diagnosing cancer, the method comprising the steps of: (a) detecting ionized fragments of cancer-specific VOCs, which have molecular weights of (i) 69, (ii) 131 and (iii) 181, in exhaled breath gas; and (b) acquiring cancer-related information based on the results of the detection.

The present inventors have developed a method of diagnosing cancer by analyzing volatile organic compounds (VOCs) contained specifically in exhaled breath of cancer patients and detecting the volatile organic compounds.

In an example of the present invention, an electronic nose and GC-MS were used for the detection of VOCs in exhaled breath. However, any analytical instrument may be used in the present invention without limitation, as long as it can detect certain VOCs in exhaled breath.

The electronic nose digitizes the olfactory sense of a human nose, is based on multi-sensor array technology, and displays an electrical signal from the electrochemical reaction of a certain fragrant or odor component with each sensor. In the present invention, the electron nose Smart Nose 300 (Switzerland) connected with a mass spectrometer was used.

In the present invention, the electronic nose may be equipped with a mass spectrometer, and the detection of the ionized VOC fragments in exhaled breath gas may be performed using the mass spectrometer equipped in the electronic nose.

In addition, in the present invention, the detection of the ionized VOC fragments in exhaled breath gas may be performed using an instrument selected from the group consisting of an electronic nose, a gas chromatography-mass spectrometry (GC-MS) and a gas chromatography (GC) instrument.

In an example of the present invention, exhaled breath collected from breast cancer patients and normal persons was analyzed using an electronic nose, and as a result, it was found that the profile of VOCs did differ between the normal persons and the breast cancer patients. The exhaled breath was analyzed again by GC-MS. As a result, it was found that ionized fragments of VOCs, which have molecular weights of (i) 69, (ii) 131 and (iii) 181, are detected specifically in breast cancer patients.

In another example of the present invention, exhaled breath from thyroid cancer patients was analyzed by GC-MS. As a result, it was found that ionized fragments of VOCs, which have molecular weights of (i) 69, (ii) 131 and (iii) 181, were detected in the thyroid cancer patients.

In the present invention, step (a) further comprises detecting an ionized fragment of VOC, which has a molecular weight selected from the group consisting of 51, 63, 79, 101, 113, 129, 147, 151 and 199.

Thus, the cancer diagnosis method according to the present invention can diagnose a cancer selected from the group consisting of brain tumor, head and neck cancer, breast cancer, thyroid cancer, lung cancer, gastric cancer, liver cancer, pancreatic cancer, small bowel cancer, colorectal cancer, renal cancer, prostate cancer, cervical cancer, endometrial cancer and ovarian cancer.

In the present invention, the compounds corresponding to the ionized fragments having molecular weights of (i) 69, (ii) 131 and (iii) 181 may be selected from the group consisting of perfluorodecanoic acid, perfluoro-n-pentanoic acid, perfluorononanoic acid, perfluorooctanoic acid, perfluoro-1-heptene, perfluorocyclohexane, 1H,1H-perfluoro-1-heptanol, octafluorocyclobutane, perfluoro(methylcyclohexane), and mixtures thereof.

The above compounds have the following characteristics:

1) Perfluorodecanoic acid

Molecular weight: $C_{10}HF_{19}O_2$;

Molecular weight: 514.08;

CAS registry number: 335-76-2;

Formula 1

2) Perfluoro-n-pentanoic acid
Molecular formula: $C_5HF_9O_2$;
Molecular weight: 264;
CAS registry number: 2706-90-3;

Formula 2

3) Perfluorononanoic acid
Molecular formula: $C_9HF_{17}O_2$;
Molecular weight: 464;
CAS registry number: 375-95-1;

Formula 3

4) Perfluorooctanoic acid
Molecular formula: $C_8HF_{15}O_2$;
Molecular weight: 414;
CAS registry number: 335-67-1;

Formula 4

5) Perfluoro-1-heptene
Molecular formula: $C_7F_{14}$;
Molecular weight: 350;
CAS registry number: 355-63-5;

Formula 5

6) Perfluorocyclohexane
Molecular formula: $C_6F_{12}$;
Molecular weight: 300;
CAS registry number: 355-68-0;

Formula 6

7) 1H,1H-perfluoro-1-heptanol
Molecular formula: $C_7H_3F_{13}$;
Molecular weight: 350;
CAS registry number: 375-82-6;

Formula 7

8) Octafluorocyclobutane
Molecular formula: $C_4F_8$;
Molecular weight: 200;
CAS registry number: 115-25-3;

Formula 8

9) Perfluoro(methylcyclohexane)
Molecular formula: $C_7F_{14}$;
Molecular weight: 350;
CAS registry number: 355-02-2

Formula 9

In another aspect, the present invention is directed to a method for providing information for cancer diagnosis, the method comprising the steps of: (a) detecting ionized fragments of cancer-specific VOCs, which have molecular weights of (i) 69, (ii) 131 and (iii) 181, in exhaled breath gas; and (b) acquiring cancer-related information based on the results of the detection.

In still another aspect, the present invention is directed to a method for providing information for cancer diagnosis, the method comprising a step of measuring whether a cancer-specific VOC selected from the group consisting of perfluorodecanoic acid, perfluoro-n-pentanoic acid, perfluorononanoic acid, perfluorooctanoic acid, perfluoro-1-heptene, perfluorocyclohexane, 1H,1H-perfluoro-1-heptanol octafluorocyclobutane and perfluoro(methylcyclohexane) is present in exhaled breath gas collected from a patient suspected of having cancer.

In yet another aspect, the present invention is directed to a method of measuring a cancer-specific VOC for diagnosing cancer, the method comprising a step of measuring whether a cancer-specific VOC selected from the group consisting of perfluorodecanoic acid, perfluoro-n-pentanoic acid, perfluorononanoic acid, perfluorooctanoic acid, perfluoro-1-heptene, perfluorocyclohexane, 1H,1H-perfluoro-1-heptanol octafluorocyclobutane and perfluoro(methylcyclohexane) is present in exhaled breath gas collected from a patient suspected of having cancer.

In the present invention, the measurement step may be performed using an instrument selected from the group consisting of an electronic nose, a gas chromatography-mass spectrometry (GC-MS) and a gas chromatography (GC) instrument. In addition, the cancer may be selected from the group consisting of brain tumor, head and neck cancer, breast cancer, thyroid cancer, lung cancer, gastric cancer, liver cancer, pancreatic cancer, small bowel cancer, colorectal cancer, renal cancer, prostate cancer, cervical cancer, endometrial cancer and ovarian cancer.

In a further aspect, the present invention is directed to a method of diagnosing cancer by analyzing ionized fragments of cancer-specific VOCs having molecular weights of (i) 69, (ii) 131 and (iii) 181 in exhaled breath, the method comprising the steps of: (a) detecting ionized fragments of cancer-specific VOCs, which have molecular weights of (i) 69, (ii) 131 and (iii) 181, in exhaled breath gas; and (b) acquiring cancer-related information based on the results of the detection.

In a still further aspect, the present invention is directed to a method of diagnosing cancer, the method comprising a step of measuring whether a cancer-specific VOC selected from the group consisting of perfluorodecanoic acid, perfluoro-n-pentanoic acid, perfluorononanoic acid, perfluorooctanoic acid, perfluoro-1-heptene, perfluorocyclohexane, 1H,1H-perfluoro-1-heptanol octafluorocyclobutane and perfluoro(methylcyclohexane) is present in exhaled breath gas collected from a patient suspected of having cancer.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Sampling of Exhaled Breath from Cancer Patients and Analysis of Exhaled Breath Samples by Electronic Nose Exhaled breath of breast cancer patients was collected immediately before surgery from hospitalized patients who were diagnosed as breast cancer in the Breast Cancer Center of Konkuk University Hospital (Korea) and who did not undergo breast cancer surgery. Exhaled breath of breast cancer patients was collected from 62 patients, and exhaled breath of healthy persons was collected from 1,000 healthy consumers by stem cell counselors of RNL Bio.

As exhaled breath, an alveolar breath portion was sampled from each of breast cancer patients and healthy persons by use of a breath sampling bag (0.5-liter breath sampling bag for analysis of *H. pylori*, Otsuka Pharmaceutical Co., Ltd., Japan). As breast cancer patient from which exhaled breath was to be sampled, patients, who were diagnosed as breast cancer by other diagnostic method and did not undergo breast cancer surgery, were selected. The exhaled breath collected in the breath sampling bag was analyzed using an electronic nose (SMart Nose 300, Smart Nose, Marin-Epagnier, Switzerland), and signal patterns detected by the sensor of the electronic nose were analyzed by a pattern recognition algorithm software, thereby a difference in the pattern between the breath samples of the cancer patients and the breath samples of the healthy control group.

100 mL of the exhaled breath sample from each of the breast cancer patients and the healthy control group was trapped in an index syringe and adsorbed.

The adsorbed sample was injected into the electronic nose in a state in which the inlet temperature of the electronic nose was 200° C. For injection of the sample, nitrogen (99.999%) was run at a flow rate of 230 ml/min. Data were collected for 3 minutes, and after analysis, purge was performed for 3 minutes. In addition, purge between the samples was also performed for 3 minutes.

The electronic nose (SMart Nose 300, Smart Nose, Marin-Epagnier, Switzerland) used in the analysis had a quadrupole mass spectrometer (Balzers Instruments, Marin-Epagnier, Switzerland) connected thereto. Volatile compounds were ionized at 70 eV, and the ionized compounds were passed through a quadrupole mass filter for 180 seconds, after which compounds falling within a certain mass range (10-200 amu) were measured in integer units to determine the number of channels. The channel number was 190 (10-200 amu).

Figure 1:
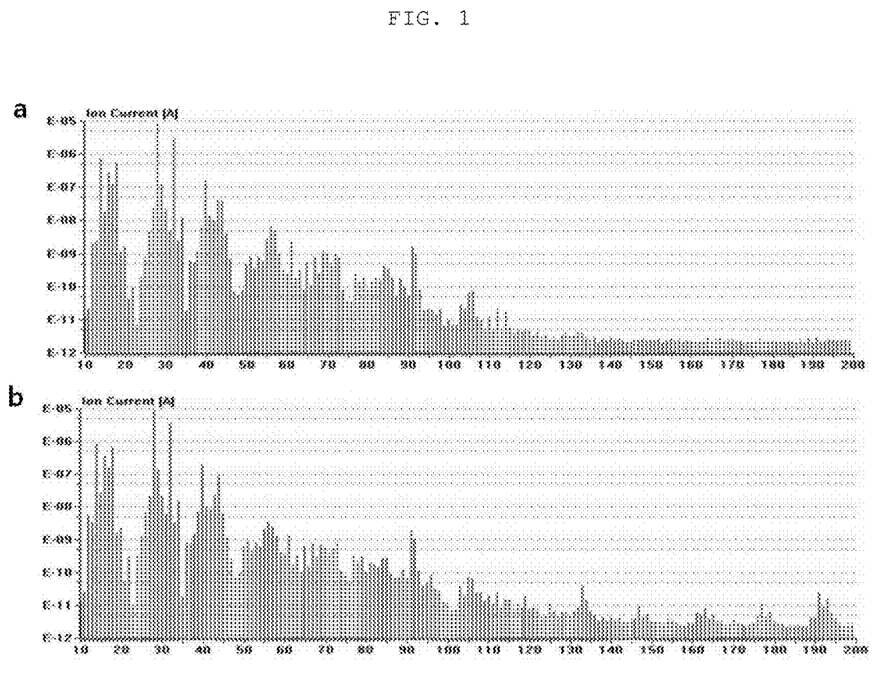
FIG. 1 shows the results of analyzing volatile organic compounds (VOCs), contained in exhaled breath of normal persons and breast cancer patients, by use of an electronic nose. (a): results for compounds contained in exhaled breath of a healthy control group; and (b): results for compounds contained in exhaled breath of breast cancer patients.

The results of the measurement are shown in FIG. 1. As can be seen in FIG. 1, molecular weight values discriminative between the healthy control group and the breast cancer group could be found. The discriminative molecular weights were 51, 63, 69, 79, 93, 101, 113, 129, 131, 147, 151, 161, 181, 199, etc.

In order to find fragments having the above molecular weights (molecular weights in the masses of fragmented ions, molecular ions, etc., which are produced when ionizing samples by electron impact or ionic molecular reactions in mass spectrometry and have a certain mass/charge (m/e) ratio), the exhaled breath of each of the healthy control group and the breast cancer group was analyzed again by GC-MS.

Example 2: GC-MS Analysis of Exhaled Breath of Breast Cancer Patients

The exhaled breath collected in the breath sampling bag according to the method of Example 1 was adsorbed onto SPME (Solid-Phase microextraction) fiber for 20 minutes, and the SPME fiber adsorbed with the exhaled breath was injected into a GC-MS (Shimadzu GC 2010, GCMS QP2010 Plus). The oven program used in GC was as follows: 5 min at 40° C., heating to 300° C. at a rate of 10° C./min, and then 3 min at 300° C. The column used was HP—5% phenyl methyl siloxane (30 m length, 0.25 mm I.D., 0.25 μm thickness). The column pressure was 57.4 kPa, and the flow rate was 1.11 ml/min. In addition, information database used for identification of compounds was NIST/EPA/NIH.

Figure 2:
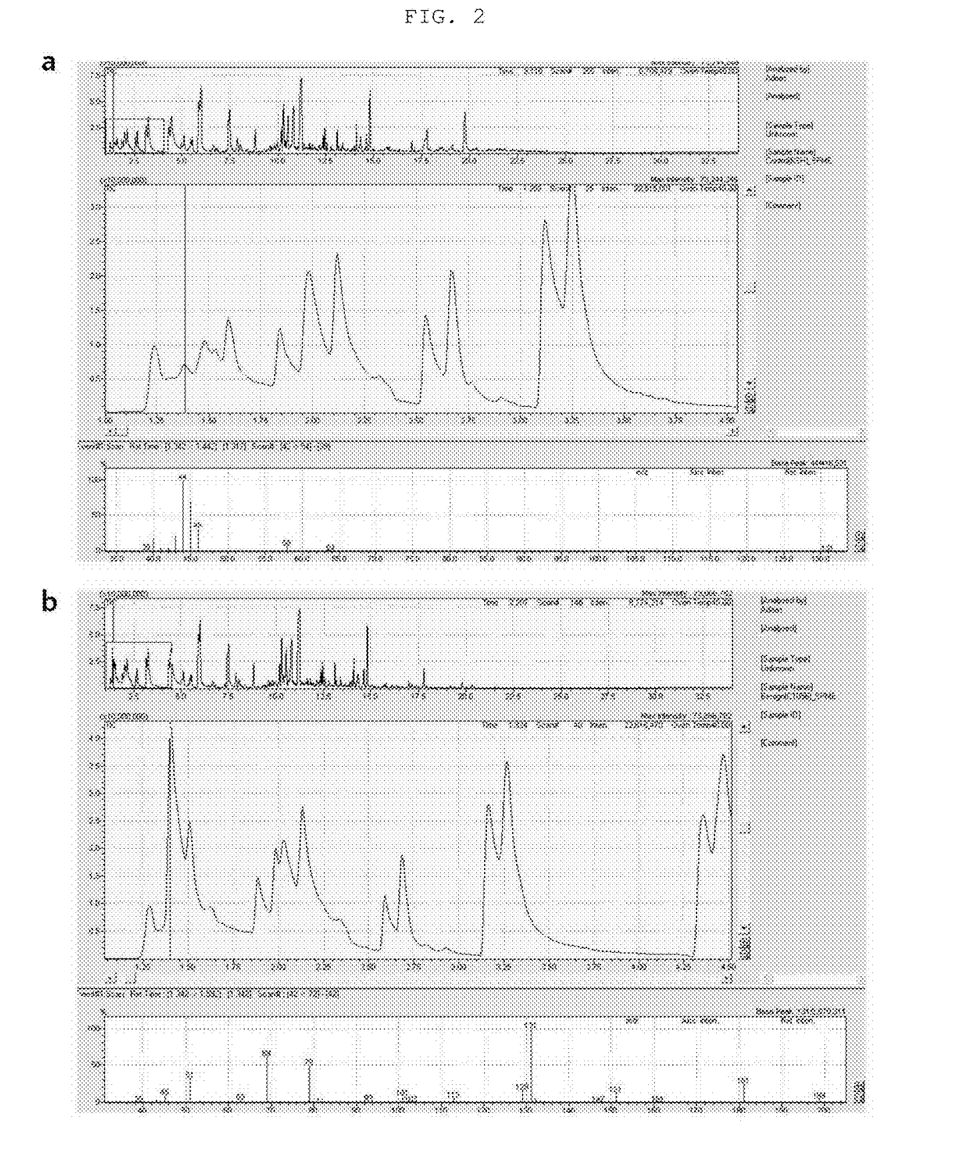
FIG. 2 shows the results of analyzing volatile organic compounds (VOCs), contained in exhaled breath of normal persons and breast cancer patients, by gas chromatography-mass spectrometry (GC-MS). (a): results for compounds contained in exhaled breath of a healthy control group; and (b): results for compounds contained in exhaled breath of breast cancer patients.
Figure 3:
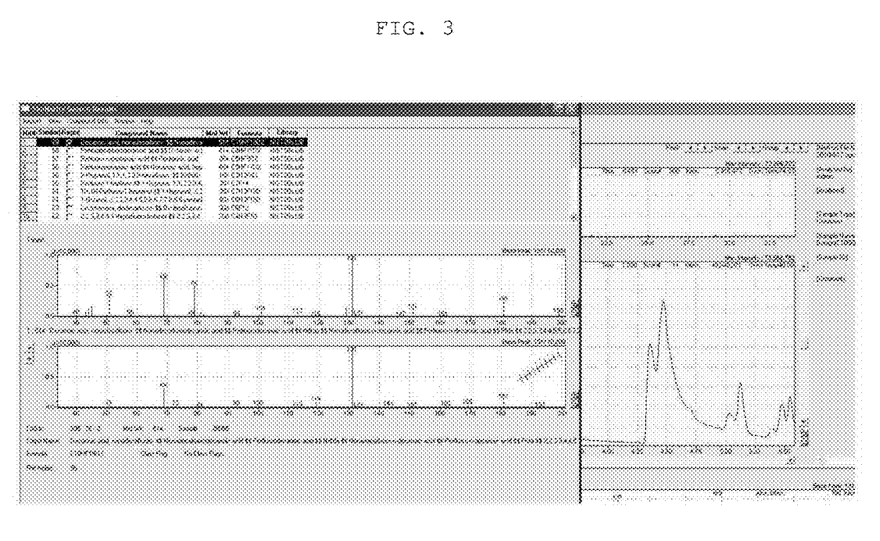
FIG. 3 shows a method of analyzing GC-MS results for exhaled breath samples of breast cancer patients by use of a database.

The results of the analysis are shown in FIG. 2. As can be seen therein, fragments having molecular weights of 69, 131 and 181 were detected specifically in the exhaled breath of the cancer patients.

In order to identify the volatile organic compounds detected as fragments having molecular weights of 69, 131 and 181 in GC-MS and present in the exhaled breath of the cancer patients, the volatile organic compounds were analyzed using NIST/EPA/NIH. As a result, the volatile organic compounds were determined to be the compounds of formula 1 to formula 9 having the following characteristics:

The above compounds have the following characteristics:

1) Perfluorodecanoic acid
Molecular weight: $C_{10}HF_{19}O_2$;
Molecular weight: 514.08;
CAS registry number: 335-76-2;

Formula 1

2) Perfluoro-n-pentanoic acid
Molecular formula: $C_5HF_9O_2$;
Molecular weight: 264;
CAS registry number: 2706-90-3;

Formula 2

3) Perfluorononanoic acid
Molecular formula: $C_9HF_{17}O_2$;
Molecular weight: 464;
CAS registry number: 375-95-1;

Formula 3

4) Perfluorooctanoic acid
Molecular formula: $C_8HF_{15}O_2$;
Molecular weight: 414;
CAS registry number: 335-67-1;

Formula 4

5) Perfluoro-1-heptene
Molecular formula: $C_7F_{14}$;
Molecular weight: 350;
CAS registry number: 355-63-5;

Formula 5

6) Perfluorocyclohexane
Molecular formula: $C_6F_{12}$;
Molecular weight: 300;
CAS registry number: 355-68-0;

Formula 6

7) 1H,1H-perfluoro-1-heptanol
Molecular formula: $C_7H_3F_{13}$;
Molecular weight: 350;
CAS registry number: 375-82-6;

Formula 7

8) Octafluorocyclobutane
Molecular formula: $C_4F_8$;
Molecular weight: 200;
CAS registry number: 115-25-3;

Formula 8

9) Perfluoro(methylcyclohexane)
Molecular formula: $C_7F_{14}$;
Molecular weight: 350;
CAS registry number: 355-02-2

Formula 9

Table 1 below shows the results of tests performed by analyzing the exhaled breath of the breast cancer patients by GC-MS and detecting the fragments having molecular weights of 69, 131 and 181 in the exhaled breath to diagnose breast cancer.

TABLE 1

Blind test results for breast cancer patients

|  | Test results | Tissue examination results |
|---|---|---|
| Blind 1 | Breast cancer | FA (fibroadenoma) |
| Blind 2 | Breast cancer | FA + Lung cancer |
| Blind 3 | Breast cancer | IDC neoadjuvant breast cancer |
| Blind 4 | Breast cancer | FA (fibroadenoma) |
| Blind 5 | Breast cancer | IDC breast cancer |
| Blind 6 | Healthy | Normal |
| Blind 7 | Breast cancer | IDC breast cancer |
| Blind 8 | Breast cancer | FCC fibrocystic disease |

As can be seen in Table 1 above, the fragments having molecular weights of 69, 131 and 181 were not detected in the healthy persons, but were detected in the patients who had breast cancer or were being developed into breast cancer.

Example 3: Diagnosis of Thyroid Cancer Patients Using Exhaled Breath

Figure 4:
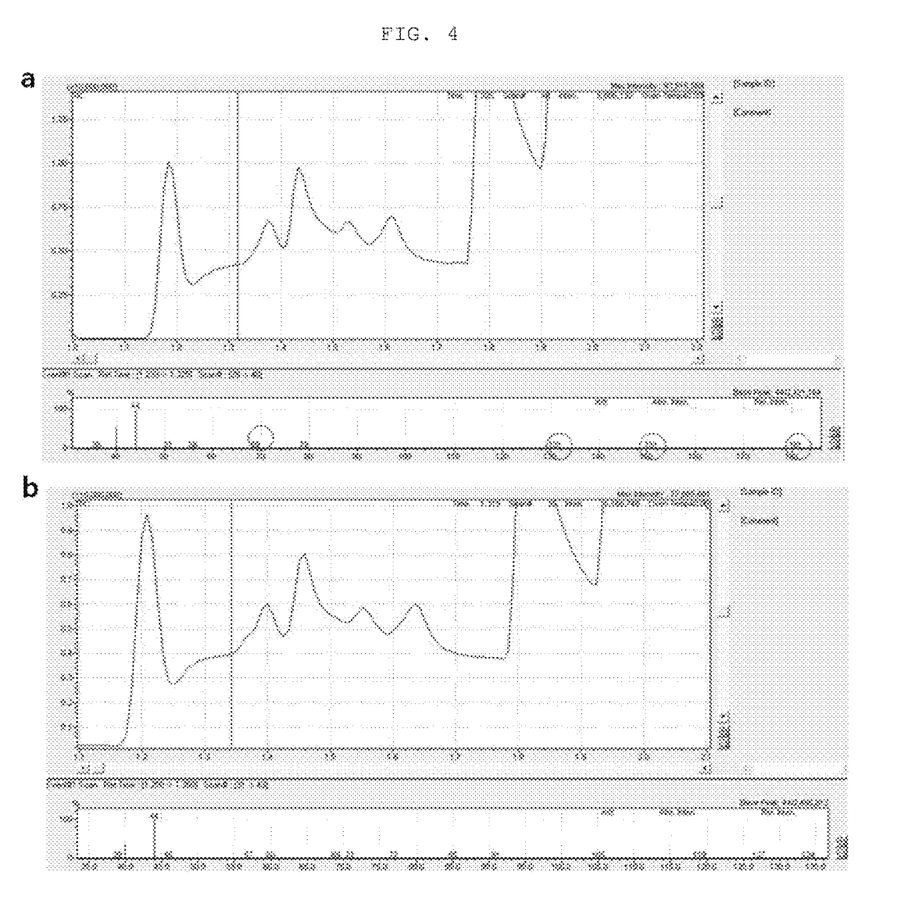
FIG. 4 shows the results of analyzing volatile organic compounds (VOCs), contained in exhaled breath of normal persons and thyroid cancer patients, by gas chromatography-mass spectrometry (GC-MS). (a): results for compounds contained in exhaled breath of thyroid cancer patients; and (b): results for compounds contained in exhaled breath of a healthy control group.

A total of 13 exhaled breath samples (3 males and 10 females) of thyroid cancer patients, received from Seoul National University Hospital (Korea), were analyzed by GC-MS, and the molecular weights of the resulting fragments were measured according to the method of Example 2. As a result, it was shown that the fragments having molecular weights of 69, 131 and 181 were detected in all the 13 samples (FIG. 4).

INDUSTRIAL APPLICABILITY

As described above, according to the present invention, cancer can be early diagnosed with high sensitivity in a non-invasive manner by use of exhaled breath sampled from cancer patients. Thus, the cancer diagnosis method of the present invention can diagnose cancer in a more cost-effective and rapid manner compared to conventional cancer diagnosis methods.

Although the present invention has been described in detail with reference to the specific features, it will be apparent to those skilled in the art that this description is only for embodiments and does not limit the scope of the present invention. Thus, the substantial scope of the present invention will be defined by the appended claims and equivalents thereof.

The invention claimed is:

1. A method of detecting breast cancer or thyroid cancer in a patient, said method comprising:
   obtaining an exhalation gas sample from a human patient;
   ionizing volatile compounds in said exhalation gas sample to form ionized fragments of said volatile compounds;
   detecting ionized fragments of molecular weights 69, 131, and 181 when present in said ionized fragments of said volatile compounds; and
   when ionized fragments of molecular weight 69, 131, and 181 are detected in said ionized fragments of said volatile compounds, analyzing said volatile compounds corresponding to said ionized fragments of molecular weight 69, 131, and 181 via an information database to detect breast cancer or thyroid cancer-specific compounds selected from the group consisting of compounds (1)-(9) and mixtures thereof, when present in said volatile compounds,
   wherein
   compound (1) is perfluorodecanoic acid,
   compound (2) is perfluoro-n-pentanoic acid,
   compound (3) is perfluorononanoic acid,
   compound (4) is perfluorooctanoic acid,
   compound (5) is perfluoro-1-heptene,
   compound (6) is perfluorocyclohexane,
   compound (7) is 1H,1H-perfluoro-1-heptanol,
   compound (8) is octafluorocyclobutane, and
   compound (9) is perfluoro(methylcyclohexane).

2. The method according to claim 1, further comprising corroborating said detecting cancer with tissue examination results.

3. The method according to claim 1, wherein said detecting ionized fragments is performed by use of an instrument selected from the group consisting of electronic noses, gas chromatography (GC) instruments, and gas chromatography-mass spectrometry (GC-MS) instruments.

4. The method according claim 1, wherein said detecting ionized fragments of molecular weights 69, 131, and 181 when present in said ionized fragments of said volatile compounds, further comprises detecting ionized fragments having molecular weight selected from the group consisting of molecular weights 51, 63, 79, 101, 113, 129, 147, 151, and 199, when present in said ionized fragments of said volatile compounds, as additional ionized fragments for detecting said cancer.

5. The method according to claim 1, wherein said exhalation gas sample comprises an alveolar breath portion of an exhaled breath of said human patient.

6. The method according claim 1, wherein said obtaining an exhalation gas sample from a human patient comprises collecting said exhalation gas sample in a breath sampling bag.

* * * * *